United States Patent [19]

Wilson

[11] Patent Number: 4,592,661
[45] Date of Patent: Jun. 3, 1986

[54] HEAT STRESS MONITOR

[75] Inventor: Bruce L. Wilson, Cheltenham, Australia

[73] Assignee: Dobbie Instruments (Australia) Pty. Ltd., West Perth, Australia

[21] Appl. No.: 672,193

[22] Filed: Nov. 16, 1984

[30] Foreign Application Priority Data

Nov. 18, 1983 [AU] Australia ............................... PG2454

[51] Int. Cl.<sup>4</sup> .......................... G01N 25/00; G01K 3/00
[52] U.S. Cl. ...................................... 374/10; 374/109; 374/190
[58] Field of Search .......................... 374/10, 109, 190; 73/336, 338

[56] References Cited

U.S. PATENT DOCUMENTS

| | | | |
|---|---|---|---|
| 2,193,519 | 3/1940 | Parsons | 374/109 |
| 2,470,188 | 5/1949 | Rhodes et al. | 73/338 |
| 3,771,364 | 11/1973 | Worthington | 73/336 |
| 3,817,102 | 6/1974 | Shea | 73/338 |
| 3,855,863 | 12/1974 | Kuehn et al. | 374/109 |

OTHER PUBLICATIONS

"Announcing the Wet Globe Thermometer," Howard Engineering Company brochure, Jun. 1970.

Primary Examiner—Robert I. Smith
Assistant Examiner—Patrick R. Scanlon
Attorney, Agent, or Firm—Finnegan, Henderson, Farabow, Garrett & Dunner

[57] ABSTRACT

A heat stress monitor comprised of a thermometer tube having at least a black globe-bulb and a wet-bulb therein and adapted to provide a direct reading of wet-bulb globe temperature (WBGT). The inclusion in the tube of a dry-bulb makes the monitor particularly adapted to measuring WBGT outdoors. The thermometer tube is in the form of a single tube and the bulbs are disposed in series therein with an extension part extending beyond the bulbs to permit a direct reading to be taken of the position of a thermally responsive medium in the tube.

11 Claims, 3 Drawing Figures

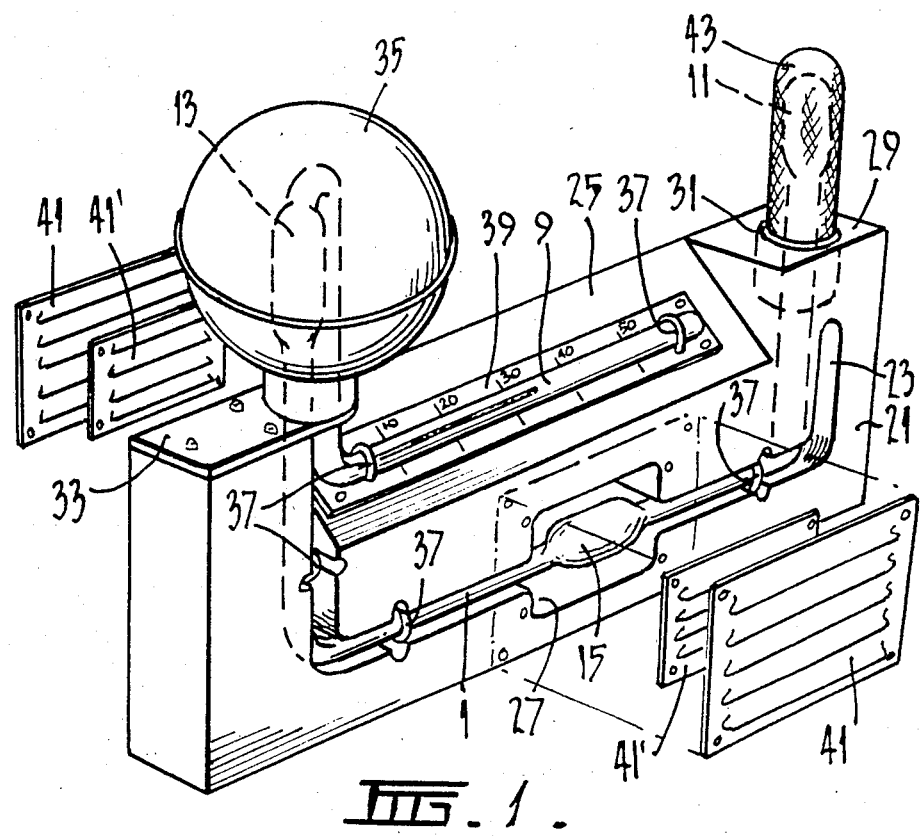

HEAT STRESS MONITOR

This invention relates to a heat stress monitor.

In order to accurately measure environmental temperature for determining efficient workload to be performed by individuals, it has been recognized that at least two temperature measurements should be obtained and suitably combined together. Such temperature measurements are a wet-bulb temperature measurement and the temperature measurements obtained inside a black globe. Sometimes, particularly when monitoring heat stress outdoors, a third temperature measurement is included. The third temperature is measured by way of a shaded dry-bulb.

These combined temperature measurements can provide a wet-bulb globe temperature measurement known as WBGT. Charts have been prepared to relate the WBGT measurement obtained to specific work related environments. Accordingly it has been possible to esitmate the work/rest periods per hour for specific labour duties.

The measurement of the WBGT has been cumbersome owing to the requirement to make two or three individual temperature measurements and then combine them. Proposals, such as that in U.S. Pat. No. 3,817,102, have been made to facilitate the determination of WBGT, but this has still required the use of three separate thermometer tubes. It has also been proposed, for example in U.S. Pat. No. 3,771,364, to provide a single thermometer stem from which the WBGT reading is directly read with two or more bulbs disposed in parallel manner at one end of the tube for measuring the required temperatures with the volumes of the bulbs being in the correct volume ratio with respect to each other so that the input of temperature response medium from the bulbs into the stem correctly indicates the WBGT. However, no such direct reading WBGT heat stress monitor has ever been successfully marketed. More recently it has been proposed, for example in U.S. Pat. No. 3,855,863, to take the respective measurements and combine them electronically to give the WBGT. Such device however is relatively expensive. To date there has been no successful direct reading WBGT index heat stress monitor in the form of a conventional thermometer.

The present invention attempts to provide such a monitor to facilitate the easy and accurate measurement of the WBGT index.

Therefore according to a first broad aspect of the present invention there is provided a heat stress monitor comprising a thermometer tube having a black globe-bulb and a wet-bulb therein, a black globe for receiving the black globe-bulb and means capable of moistening the surface of the wet-bulb, the thermometer tube being adapted to provide a direct reading of wet-bulb globe temperature, and wherein the thermometer tube comprises a single tube with the bulbs disposed in series therein and a common thermally responsive medium in the tube which medium extends from one of the bulbs, through the tube into the other bulb and beyond said other bulb into an extension part of the tube which is provided to permit a reading to be taken of the position of the thermally responsive medium, the internal volumes of the black globe-bulb and the wet-bulb being respectively proportional to the percentages of the black globe temperature and of the wet-bulb temperature required for determining the wet-bulb globe temperature whereby the position of the thermally responsive medium is indicative of the wet-bulb globe temperature.

In accordance with a further broad aspect of the present invention there is provided a heat stress monitor comprising a thermometer tube having a black globe-bulb, a dry-bulb and a wet-bulb therein, a black globe for receiving the black globe-bulb, means protecting the dry-bulb from direct solar radiation and means capable of moistening the surface of the wet-bulb, the thermometer tube being adapted to provide a direct reading of wet-bulb globe temperature, and wherein the thermometer tube comprises a single tube with the bulbs disposed in series therein and a common thermally responsive medium in the tube which medium extends from one of the bulbs, serially through the tube and the second and third bulbs and beyond said third bulb into an extension part of the tube which is provided to permit a reading to be taken of the position of the thermally responsive medium, the internal volumes of the black globe-bulb, the dry-bulb and the wet-bulb being respectively proportional to the percentages of the black globe temperature, of the dry-bulb temperature and of the wet-bulb temperature required for determining the wet-bulb globe temperature whereby the position of the thermally responsive medium is indicative of the wet-bulb globe temperature. Such an arrangement is used for outdoors heat stress monitoring, in contrast to the device in accordance with the first aspect of the invention which is particularly useful indoors.

Most preferably the dry-bulb is positioned intermediate the wet-bulb and the black globe-bulb and should be shaded from direct sunlight.

It is also particularly preferred that the monitor have the thermometer tube thereof shaped generally in a shallow U configuration, with the wet-bulb being on one free arm thereof and the black globe-bulb being on the other free arm thereof, there being an interconnection across the base of the U between the bulbs, and wherein said extension part of the thermometer tube for providing the WBGT measurement extends substantially parallel with the base of the U and is an extension of the free arm of the U which contains the black globe-bulb.

Generally, the black globe may be in the form of a VERNON globe. However, other devices such as that proposed in the aforesaid U.S. Pat. No. 3,817,102 have been designed to replace VERNON globes and are hereby included within the term "black globe".

The thermometer tube is preferably secured in a housing from which the wet-bulb and black globe-bulb project respectively inside the moistening means and the black globe and the extension part is visible externally of the housing. Advantageously the extension part is mounted on an external surface of the housing.

In order that the invention can be more clearly ascertained two preferred embodiments will now be described with reference to the accompanying drawings wherein:

FIG. 1 is a front perspective view of one preferred heat stress monitor for use in outdoor environments in sunshine;

FIG. 2 is a schematic view of the thermometer tube of the embodiment shown in FIG. 1; and FIG. 3 shows an alternative embodiment of thermometer tube for use indoors or outside but not in sunshine. The thermometer tube shown in FIG. 3 is fitted in use within a housing similar to that shown for the embodiment of FIG. 1.

Referring firstly to the embodiment shown in FIGS. 1 and 2 there is shown a thermometer tube 1 of generally shallow U-shaped configuration. The thermometer tube 1 has one free arm 3 and a further free arm 5. It has a base 7 and an extension portion 9. The extension portion 9 is an extension of the free arm 5 and runs parallel with the base 7. A wet-bulb 11 is provided on the free arm 3. A VERNON globe-bulb 13 is provided on the free arm 5. A dry-bulb 15 is provided on the base 7. It can be seen that the wet-bulb 11 is positioned at the extreme free end of the free arm 3. The VERNON globe-bulb 13 is positioned near the free end of the free arm 5. The dry-bulb 15 is positioned near the centre of the base 7.

Referring now specifically to FIG. 1 there is shown a housing 21 in which the thermometer tube 1 is received. The housing 21 is advantageously made of solid wood and has a generally U-shaped grooved recess 23 therein. The upper central portion of the housing 21 is chamfered to provide an inclined face 25. The extension portion 9 of the thermometer tube 1 extends across the inclined face 25. The central region of the U-shaped grooved recess 23 between the ends of the housing 21 is provided with an enlarged opening 27 which extends through the housing. The right hand end of the housing 21 has a bore 29 therein, in which is received a cup-shaped member 31. The left hand end of the housing 21 has a bracket member 33 screwed thereto. The bulb 11 passes through the bore 29 and through the cup-shaped member 31. The cup-shaped member 31 is sealed at its bottom around the free arm 3 of the bulb 11 with a sealant such as SILASTIC (Registered Trade Mark). The dry-bulb 15 is received within the enlarged opening 27. The VERNON globe-bulb 13 is received within a VERNON globe 35 which is screw threadably fastened onto the bracket member 33. Thermometer clips 37 are provided at various locations in the housing 21 to support the thermometer tube 1 therein. A temperature scale in WBGT ° (for example Celsius or Fahrenheit) may be provided on the inclined face 25. The scale is designated by numeral 39. The enlarged opening 27 is covered on both front and rear faces of the housing with a respective pair of louvered panels 41 and 41'. Only one louvered panel 41 need be provided in each side but the inner louvered panels 41' provide double baffle protection against incipient radiation allowing the dry-bulb 15 to more closely follow true air temperature. The inner panels 41' may be located immediately adjacent the bulb 15 within the opening 27.

It can therefore be seen that a single thermometer tube 1 extends between the wet-bulb 11, the dry-bulb 15 and the VERNON globe-bulb 13 and it continues to the extension portion 9 for providing a reading of the WBGT. The wet-bulb 11 is covered with a cloth material wick 43. The cloth material wick 43 is like a sleeve and it extends into the cup-shaped member 31.

In use, the cup-shaped member 31 is filled with water so that the wick 43 is wet. Typically the wick 43 is made of cotton. Typically the VERNON globe is 150 mm diameter and made of copper and has a black matt finish. Desirably the thermometer tube 1 is filled with mercury, however other suitable thermally responsive mediums may be used.

The internal volumes of the bulbs 11, 13 and 15 must be in the correct volume ratio with respect to each other so that the input of mercury into the extension portion 9 correctly reads the WBGT. WBGT is determined according to the following formula:

$$0.7 \text{ wet-bulb temperature} + 0.2 \text{ VERNON globe temperature} + 0.1 \text{ dry-bulb temperature} = \text{WBGT}.$$

Thus the wet-bulb 11 has a volume ratio of 70%, the VERNON globe-bulb 13 has a volume ratio of 20% and the dry-bulb 15 has a volume ratio of 10%. In order to calibrate the monitor, the thermometer tube 1 is inserted in a liquid bath such as that of water and the water is heated to a temperature of say 30° C. A calculation is then made knowing the volumes of the respective bulbs 11, 13 and 15 knowing the final temperature. Because the wet bulb is 70% volume it will provide a temperature influence on the thermometer tube 1 representing 70% of the temperature of the liquid i.e. 30° C. That, in turn, equals a reading of 21° C. The VERNON globe bulb will provide a 20% reading equal to 6° C. and the dry-bulb will provide a 10% reading representing a reading of 3° C. Accordingly when the temperature of the bath is at 30° C. the total temperature indicated will be a temperature of 21°+6°+3°=30°. Similar calculations are made for various temperatures of the bath and the monitor is appropriately calibrated.

In use, the monitor is situated in a work environmental position and a temperature measurement made. That temperature measurements is the WBGT in °C. and the value obtained is then checked against a known chart to ascertain the work/rest duty ratios for workers in that environment. Different types of work i.e. manual work as against clerical work have different work/rest ratios.

Referring now to the embodiment shown in FIG. 3, it is identical to that shown in FIGS. 1 and 2 except that there is no dry-bulb. Accordingly the embodiment of FIG. 3 is suitable for use indoors or outside but not in sunshine. Here, the volume ratio of the wet-bulb 11 is 70% and the volume ratio of the VERNON globe-bulb 13 is 30% since WBGT monitored in enclosed spaces in which non-solar radiation may be involved is determined according to the formula:

$$0.7 \text{ wet-bulb temperature} + 0.3 \text{ VERNON globe temperature} = \text{WBGT}.$$

The thermometer tube 1 is fitted within a similar housing to that shown in the embodiment of FIGS. 1 and 2 except that it does not need to have the enlarged opening 27 or the pairs of louvered panels 41 and 41'.

Typically the scale 39 is calibrated between 0° C. and 50° C. across the length thereof.

Modifications may be made to the present invention as would be apparent to persons skilled in the thermometer manufacturing arts. These and other modifications may be made without departing from the ambit of the invention the nature of which is to be determined from the appended claims.

I claim:

1. A heat stress monitor comprising a thermometer tube shaped generally in a shallow U configuration and having a black globe-bulb on one free arm thereof and a wet-bulb on the other free arm thereof, there being an interconnection across the base of the U between the bulbs so as to connect said bulbs in series, a black globe for receiving the black globe-bulb and means capable of moistening the surface of the wet-bulb, the thermometer tube being adapted to provide a direct reading of wet-bulb globe temperature, and a common thermally responsive medium in the tube which medium extends from the wet-bulb through the tube into the black globe-bulb and beyond said black globe-bulb into an extension part of the tube which extends substantially parallel with the base of the U and is provided to permit a reading to be taken of the position of the thermally responsive medium, the internal volumes of the black globe-bulb and the wet-bulb being respectively proportional to the percentages of the black globe temperature and of the wet-bulb temperature required for determining the wet-bulb globe temperature whereby the position of the thermally responsive medium is indicative of the wet-bulb globe temperature.

2. A heat stress monitor according to claim 1 wherein the thermometer tube is secured in a housing from which the wet-bulb and black globe-bulb project respectively inside the moistening means and the black globe and the extension part is visible externally of the housing.

3. A heat stress monitor according to claim 2 wherein the extension part is mounted on an external surface of the housing.

4. A heat stress monitor according to claim 2 wherein the moistening means comprises a cup mounted in the housing and a liquid absorbent sheath extending from the cup around the wet-bulb.

5. A heat stress monitor comprising a thermometer tube having a black globe-bulb, a dry-bulb and a wet-bulb therein, a black globe for receiving the black globe-bulb, means protecting the dry-bulb from direct solar radiation and means capable of moistening the surface of the wet-bulb, the thermometer tube being adapted to provide a direct reading of wet-bulb globe temperature, and wherein the thermometer tube comprises a single tube with the bulbs disposed in series therein and a common thermally responsive medium in the tube which medium extends from the wet-bulb, serially through the tube, through the dry-bulb and into the black globe-bulb and beyond said black globe-bulb into an extension part of the tube which is provided to permit a reading to be taken of the position of the thermally responsive medium, the internal volumes of the black globe-bulb, the dry-bulb and the wet-bulb being respectively proportional to the percentages of the black globe temperature, of the dry-bulb temperature and of the wet-bulb temperature required for determining the wet-bulb globe temperature whereby the position of the thermally responsive medium is indicative of the wet-bulb globe temperature.

6. A heat stress monitor according to claim 5 wherein the thermometer tube is shaped generally in a shallow U configuration, with the wet-bulb being on one free arm thereof and the black globe-bulb being on the other free arm thereof, there being an interconnection across the base of the U between said bulbs and incorporating the dry-bulb, and wherein said extension part of the thermometer tube for providing the wet-bulb globe temperature measurement extends substantially parallel with the base of the U and is an extension of the free arm of the U which contains the black globe-bulb.

7. A heat stress monitor according to claim 5 wherein the thermometer tube is secured in a housing from which the wet-bulb and black globe-bulb project respectively inside the moistening means and the black globe and the extension part is visible externally of the housing.

8. A heat stress monitor according to claim 7 wherein the extension part is mounted on an external surface of the housing.

9. A heat stress monitor according to claim 7 wherein the moistening means comprises a cup mounted in the housing and a liquid absorbent sheath extending from the cup around the wet-bulb.

10. A heat stress monitor according to claim 7 which includes an enlarged opening in the housing and adapted to receive the dry-bulb therein and air permeable closure means preventing entry of incipient radiation to the opening.

11. A heat stress monitor according to claim 10 in which the closure means comprises a pair of overlying louvered panels.

* * * * *